United States Patent [19]

Vora et al.

[11] Patent Number: 4,663,493
[45] Date of Patent: May 5, 1987

[54] PROCESS FOR THE DEHYDROGENATION OF HYDROCARBONS

[75] Inventors: Bipin V. Vora, Elk Grove Village; Roy C. Berg, Park Ridge; Norman H. Scott, Arlington Heights, all of Ill.

[73] Assignee: UOP Inc., Des Plaines, Ill.

[21] Appl. No.: 744,075

[22] Filed: Jun. 12, 1985

Related U.S. Application Data

[63] Continuation-in-part of Ser. No. 656,426, Oct. 2, 1984, abandoned, and Ser. No. 678,952, Dec. 6, 1984, abandoned, said Ser. No. 656,426, is a continuation of Ser. No. 502,361, Jun. 8, 1983, abandoned.

[51] Int. Cl.$^4$ .................. C07C 5/333; C07C 5/42
[52] U.S. Cl. .................. 585/655; 585/314; 585/324; 585/441; 585/656; 585/660; 585/661
[58] Field of Search .................. 585/314, 324, 655, 656, 585/660, 661, 441, 442, 443, 444, 445, 323

[56] References Cited

U.S. PATENT DOCUMENTS

| | | | |
|---|---|---|---|
| 2,580,002 | 12/1951 | Carrier | 585/257 |
| 3,267,170 | 8/1966 | Aldridge et al. | 585/656 |
| 3,321,545 | 5/1967 | Rigney et al. | 585/656 |
| 3,792,110 | 2/1974 | Senn, III et al. | 585/659 |
| 4,133,842 | 1/1979 | Anderson | 585/660 |

Primary Examiner—Asok Pal
Attorney, Agent, or Firm—Thomas K. McBride; John F. Spears, Jr.

[57] ABSTRACT

A process for dehydrogenating dehydrogenatable hydrocarbons is disclosed in which a heat providing stream is utilized to supply a portion of the endothermic heat requirement of the reaction zone feed thereby decreasing the temperature drop of the dehydrogenation zone material. As a result, the amount of deleterious side reactions such as thermal cracking is reduced, and an increase in conversion of the dehydrogenatable hydrocarbons is realized.

2 Claims, 3 Drawing Figures

PROCESS FOR THE DEHYDROGENATION OF HYDROCARBONS

CROSS-REFERENCE RELATED APPLICATIONS

This application is a continuation-in-part of copending applications Ser. No. 656,426 filed Oct. 2, 1984, now abandoned, and Ser. No. 678,952 filed Dec. 6, 1984 now abandoned. All of the teachings of these prior applications are specifically incorporated herein by reference. Application Ser. No. 656,426 in turn in a continuation of application Ser. No. 502,361 filed June 8, 1983, now abandoned.

BACKGROUND OF THE INVENTION

The present invention is directed toward an improved process for the dehydrogenation of dehydrogenatable hydrocarbons. More particularly, the described inventive technique is an improved means of providing heat of reaction to a catalytic dehydrogenation reaction zone, reducing the magnitude of the temperature drop in the reaction zone and providing a higher per pass conversion of dehydrogenatable hydrocarbons to their corresponding olefins.

Dehydrogenating hydrocarbons is an important commercial hydrocarbon conversion process because of the great demand for dehydrogenated hydrocarbons for the manufacture of various chemical products such as detergents, high octane motor fuels, pharmaceutical products, plastics, synthetic rubbers, and other products well known to those skilled in the art.

In a typical hydrocarbon dehydrogenation process, the feed hydrocarbons are admixed with hydrogen and the resulting admixture is heated by indirect heat exchange with the dehydrogenation reaction zone effluent. After being heated in the feed-effluent heat exchanger, the feed stream is further heated by passage through a heater which is typically a fired heater or furnace. The admixture, typically referred to as the combined feed, is then contacted with a bed of dehydrogenation catalyst, which may exist as a fixed bed, a fluidized bed, or a movable bed via gravity flow. The resulting dehydrogenation zone effluent is withdrawn from the reaction zone and, after indirect heat exchange with the combined feed, it is passed to product separation facilities. Generally, the product separation facilities are employed to produce a gas stream, comprising substantially hydrogen, a portion of which may be recycled back to the catalytic reaction zone to provide hydrogen for admixture with the hydrogenatable hydrocarbon feed stream. Generally, a first product stream is produced comprising the desired product olefins and a second product stream comprising light hydrocarbons, typically known as light hydrocarbon by-products, having fewer carbon atoms per molecule than the desired product olefin. Both of these product streams may be recovered in the product separation facilities. In addition, a recycle stream comprising unconverted dehydrogenatable feed hydrocarbons may be withdrawn from the product separation facilities and recycled back into the combined feed stream. Fundamental to the catalytic dehydrogenation process is the fact that the dehydrogenation reaction is highly endothermic which results, as the reaction proceeds, in cooling the reactants to temperatures at which the dehydrogenation reaction will not proceed at any appreciable rate. To counteract this problem, additional heat must be supplied to the bed of dehydrogenation catalyst to assure reaction rates sufficient to make a commercial process economically feasible. Accordingly, many methods of supplying this additional heat have been contrived in order to make catalytic dehydrogenation a viable commercial process.

OBJECTS AND EMBODIMENTS

A principal object of our invention is to provide an improved process for dehydrogenating dehydrogenatable hydrocarbons to produce the corresponding olefins. A corollary object is to minimize the temperature drop of the reactants in the dehydrogenation reaction zone and thereby provide higher conversion per pass of the dehydrogenatable hydrocarbons to their corresponding olefins. Other objects in applying the invention include a more efficient use of fuel for heating the dehydrogenation zone reactants and a decrease in undesirable side reactions. Accordingly, a broad embodiment of the present invention is directed toward a process for dehydrogenating dehydrogenatable hydrocarbons comprising the steps of (a) heating a stream of dehydrogenatable hydrocarbons, a $H_2$ rich stream and a $H_2$ deficient stream hereinafter referred to as a heat providing stream; (b) contacting the thusly heated dehydrogenatable hydrocarbon stream, $H_2$ rich stream and heat providing stream with dehydrogenation catalyst in the reaction zone at dehydrogenation conditions to produce a dehydrogenation reaction zone effluent.

In an alternative and more specific embodiment, the present invention provides for (a) heating the hydrogenatable hydrocarbons and a $H_2$ rich stream to a temperature less than the dehydrogenation reaction inlet temperature; (b) hydrogenating a stream of $H_2$ deficient hydrogenatable hydrocarbons in the presence of a hydrogenation catalyst; (c) utilizing the hydrogenated $H_2$ deficient stream of hydrogenatable hydrocarbons hereinafter referred to as a heat providing stream to raise the temperature of the dehydrogenatable hydrocarbons and $H_2$ rich stream to the dehydrogenation reaction zone inlet temperature; (d) contacting the thusly heated dehydrogenatable hydrocarbons and $H_2$ rich stream, and the heat providing stream, with dehydrogenation catalyst in the reaction zone at dehydrogenation conditions to produce a dehydrogenation reaction zone effluent.

These, as well as other embodiments of the present invention, such as feedstock descriptions, catalysts and operating conditions, will become evident from the following, more detailed description.

INFORMATION DISCLOSURE

The prior art recognizes a myriad of catalyst and process descriptions for the dehydrogenation of hydrocarbons. U.S. Pat. No. 3,531,543 (Clippinger et al.) discloses dehydrogenating hydrocarbons with an essentially halogen free catalyst comprising platinum, tin and a neutralized metal oxide carrier. The preferred carriers are oxide materials whose intrinsic acidity is substantially neutralized by an alkali or alkaline earth metal component. The U.S. Pat. No. 3,531,543 patent does not teach or disclose the introduction of a heat providing stream into the dehydrogenation reaction zone.

U.S. Pat. No. 4,430,517 (Imai et al.) discloses a process for the dehydrogenation of paraffin hydrocarbon which utilizes a catalyst comprising a platinum group metal component, a tin component, an alkali or alkaline earth component and a halogen component wherein the atomic ratio of said alkali or alkaline earth component to the platinum group metal component is greater than 10 and the halogen content ranges from about 0.2 to about 15 weight percent. The U.S. Pat. No. 4,430,517 patent also does not teach or disclose the introduction of a heat providing stream into the dehydrogenation reaction zone.

Other disclosures do present varied schemes to overcome the endothermic nature of catalytic dehydrogenation and thus assuring that sufficient heat is present within the reaction zone to allow the dehydrogenation reaction to proceed at acceptable levels. One such method of supplying the necessary heat of reaction is to remove the reactants from the reaction zone and to heat them externally through the use of a heater. In such a situation, the reactants which emerge from the first bed of dehydrogenation catalyst are passed through a heater which may be associated with the reaction zone charge heater. The resulting heated reactants are then returned to the reaction zone wherein they are passed through a second bed of dehydrogenation catalyst. This sequence of alternately heating the reactants and then recontacting them with catalysts may be repeated as many times as desired. Such a process for dehydrogenating light hydrocarbons utilizing interstage reheating of the reactants is described in U.S. Pat. No. 4,376,225 (Vora), issued Mar. 8, 1983. This reference further discloses the use of hydrogen oxidation in conjunction with the interstage reheating of the reactants.

U.S. Pat. No. 2,959,626 (Krause et al.) issued Nov. 8, 1960, also discloses a process in which interstage reheating of the reactants is utilized to assure sufficient heat of reaction within the catalytic reaction zone. However, this reference does not teach or disclose the use of either a $H_2$ rich stream or of a heat providing stream.

Another method of assuring sufficient available heat of reaction within a catalytic dehydrogenation reaction zone is the introduction of superheated steam which may be admixed into the feed stream to the first catalyst bed and/or to each subsequent catalyst bed. This type of interstage reheating is normally associated with the dehydrogenation of alkylaromatic hydrocarbons and is described in U.S. Pat. No. 3,515,766 (Root et al.), issued June 2, 1970. It is also known in the prior art to pass oxygen into a catalytic dehydrogenation zone for the purpose of selectively reacting the oxygen with hydrogen released during the dehydrogenation reaction, thereby liberating heat and to consume hydrogen. As mentioned above, such a process is disclosed in U.S. Pat. No. 4,376,225 (Vora), issued Mar. 8, 1983. Such a process utilizes a hydrogen oxidation catalyst in an attempt to selectively oxidize the hydrogen rather than to oxidize the feed or product hydrocarbons also present in the dehydrogenation zone. For instance, U.S. Pat. No. 3,437,703 (Reitmeier et al.), issued Apr. 8, 1969, discloses a dehydrogenation process which may utilize either a "homogeneous catalyst system" in which oxidation and dehydrogenation catalysts are admixed or a layered system of individual catalyst beds referred to as a "multi-bed" system. This reference indicates that the process may be utilized in the dehydrogenation of butane. It appears that in this reference the feed stream to the dehydrogenation zone always comprises an admixture of the feed hydrocarbon and steam or an admixture of the feed hydrocarbons, steam and oxygen, with apparently no disclosure of the recycling of hydrogen to the dehydrogenation zone.

An alternative to the above processes which utilize the selective oxidation of hydrogen to provide the heat of reaction for the catalytic dehydrogenation of hydrocarbons is the process disclosed in U.S. Pat. Nos. 3,580,961 (Guth et al.), issued May 25, 1971, and 3,586,732 (Guth et al.) issued June 22, 1971. These references disclose a process for dehydrogenating hydrocarbons, in particular, propane, by utilizing the effluent from an oxidation-reaction zone to assure sufficient available heat of reaction for the dehydrogenation reaction. In these references, it is disclosed that a fuel gas may be derived from a deethanizer fractionating column and passed to the oxidation reaction zone in order to supply additional quantities of hydrocarbon for oxidation.

Of further interest is U.S. Pat. No. 3,847,986 (Hughes), issued Nov. 12, 1974. This reference discloses a process for dehydrogenating ethylbenzene to produce styrene. The styrene is produced by passing a mixture of ethylbenzene and super-heated steam over a suitable dehydrogenation catalyst. A quantity of fuel gas (typically having a high methane content) is admixed with the steam prior to super-heating to serve as a diluent and heat carrier. The high methane content fuel gas is then separated from the reaction zone effluent and is recovered as a vent gas. The reference goes on to disclose that the vent gas may, in turn, be recycled back to a fired heater utilized to produce steam. The reference does disclose the advantage of using a fuel gas as a heat source in that it has an appreciable higher heat capacity than steam at the operating temperatures and pressures normally utilized in dehydrogenation reactions. Moreover, as a diluent, the fuel gas acts to reduce the hydrogen partial pressure in the reaction zone resulting in increased conversion of ethylbenzene to styrene. The reference does not disclose the addition or recycle of a $H_2$ rich stream into the dehydrogenation reaction zone.

In brief summation, the prior art which employs inter-catalyst bed reheating of the reactants, selective oxidation of hydrogen, injection of steam, oxidation of fuel gas, and/or injection of fuel gas to provide the requisite heat of reaction for catalytic dehydrogenation is not cognizant of the technique described herein which employs the introduction of a stream of dehydrogenatable hydrocarbons, a $H_2$ rich stream and a heat providing stream preferably being $H_2$ deficient and containing hydrogenatable hydrocarbons, which is utilized to provide part of the requisite heat of reaction to allow the catalytic dehydrogenation reaction to proceed at an acceptable rate.

SUMMARY OF THE INVENTION

To reiterate briefly, the process encompassed by our inventive concept is suitable for use in the catalytic dehydrogenation of dehydrogenatable hydrocarbons. More particularly, the present invention is advantageously utilized to provide part of the required heat of reaction for effecting the dehydrogenation of the dehydrogenatable hydrocarbons to their corresponding olefins. By means of the present invention, it is possible to minimize the temperature drop of the reactants in the dehydrogenation reaction zone and thereby provide higher per pass conversion of the dehydrogenatable hydrocarbons. In addition, the invention results in a more efficient use for fuel for heating the reaction zone reactants and a decrease in undesirable side reactions.

The term "dehydrogenatable hydrocarbons" as utilized herein is meant to refer to all classes of hydrocarbons containing saturated carbon bonds which have the potential for forming one or more unsaturated bonds through the process of dehydrogenation. The preferred dehydrogenatable hydrocarbons of the present invention consists of paraffinic type hydrocarbons. More specifically, the paraffin hydrocarbon charge stock of the present invention may contain from 3 carbon atoms to about 30 carbon atoms. Representative members of this class are: propane, butane, pentane, hexane, heptane, nonane, decane, undecane, dodecane, tridecane, tetradecane, pentadecane, hexadecane, heptadecane, octadecane, eicosane and mixtures thereof. A particularly important class of charge stocks include propane, butane, pentane and mixtures thereof and which are readily prepared by the fractionation of relatively low boiling point hydrocarbon fractions. Another important charge stock contains normal paraffins of about 10 to about 15 carbon atoms since these produce mono-olefins which can be utilized to make detergents having superior biodegradability and detergency. For example, a mixture containing a 4 or 5 homologue spread, such as $C_{11}$ to $C_{14}$, $C_{10}$ to $C_{13}$, $C_{11}$ to $C_{15}$, provides an excellent charge stock. Moreover, it is preferred that the amount of non-normal hydrocarbon present in this normal paraffin stream be kept at low levels. Thus, it is preferred that this stream contain greater than 90 weight percent normal paraffin hydrocarbons, with best results achieved at purities in the range of 96 to 99 weight percent or more. Typically, the feed dehydrogenatable hydrocarbons to a catalytic dehydrogenation process contains admixed therewith contaminants typically comprising hydrogen, light hydrocarbons having less carbon atoms per molecule than the desired feed dehydrogenatable hydrocarbon. Accordingly, the feed to a catalytic propane dehydrogenation process may contain methane, ethane, and trace amounts of hydrogen. Although the presence of such contaminants may be disadvantageous in the past practices of catalytic dehydrogenation, the present invention employs such contaminants as well as the by-products of disadvantageous secondary reactions in the dehydrogenation zone to advantage as will be more fully set forth hereafter.

In addition to the dehydrogenatable hydrocarbons, the combined feed to the reaction zone in the present comprises a $H_2$ rich stream, preferably containing at least 75 mole percent $H_2$. The presence of $H_2$ within the reaction zone serves several purposes. First, the $H_2$ acts to suppress the formation of hydrocarbonaceous deposits on the surface of the catalyst, more typically known as coke. Secondly, $H_2$ acts to suppress thermal cracking which is an undesirable side reaction. Third, the heating of the $H_2$ rich stream prior to their introduction into the reaction zone assures more available heat to satisfy part of the heat of reaction requirements of the dehydrogenation reaction. Because $H_2$ is generated in the dehydrogenation reaction and comprises a portion of the effluent, the $H_2$ rich stream introduced into the reaction zone generally comprises recycle $H_2$ derived from separation of the reaction zone effluent. However, it is, of course, possible to use $H_2$ from other suitable sources without resorting to the use of the $H_2$ in the reaction zone effluent.

In addition to the dehydrogenatable hydrocarbon and $H_2$ rich streams, the combined feed to the reaction zone contains a third stream herein specified as a heat providing stream. This heat providing stream may be derived from a number of sources and may be utilized in a variety of ways as will be revealed herein. The heat providing stream typically comprises components having less carbon atoms per molecule than the desired olefin product. Also, the heat providing stream may contain hydrogenatable hydrocarbons, preferably unsaturated aliphatic hydrocarbons. In addition, the heat providing stream may be hydrogen deficient, preferably containing less than 5 mole percent of hydrogen. A source of the heating providing stream may include the light hydrocarbon by-products of the dehydration reaction which are separated, recovered, and recycled back to the reaction zone. Another source of the heat providing stream may include thermal pyrolysis products, preferably containing olefins having less carbon atoms per molecule than the feed dehydrogenatable hydrocarbons. The reacted thermal pyrolysis products may be separated from the dehydrogenation reaction zone effluent and recycled back to the thermal pyrolysis process to provide a portion of the heat providing stream.

Prior to introduction into the catalytic dehydrogenation zone, the dehydrogenatable hydrocarbon stream, $H_2$ rich stream and the heat providing stream must be heated. Generally, a major portion of the heat utilized to heating the dehydrogenatable hydrocarbon stream, $H_2$ rich stream, and the heat providing stream will be supplied by a furnace, typically a gas-fired or oil-fired furnace. However, because of the quantities of heat within the reaction zone effluent and the temperature differential between the reaction zone effluent and the feed streams, it has become common practice to subject the feed streams to indirect heat exchange with the reaction zone effluent in order to preheat the streams. Accordingly, after subjecting the feed streams to such preheating indirect heat exchange step, they are passed to the charge furnace for heating to a temperature equal to or less than that required for the dehydrogenation reaction. When heating to less than the required dehydrogenation temperature, the amount of thermal cracking of the dehydrogenatable hydrocarbons is reduced. The net result is increased yield of the desired product olefin.

After heating, the dehydrogenatable hydrocarbon stream, $H_2$ rich stream and the heat providing stream are introduced into the dehydrogenation reaction zone for contact with the dehydrogenation catalyst. These streams may be introduced into the reaction zone in any acceptable fashion. For example, if desired, they may be introduced as an admixture, or separately. Paraffin dehydrogenation is an endothermic reaction and the approximate heat of reaction for the formation of a mono-olefin is approximately 30 kilocalories/gram mole for a feed that may vary from $C_3$ (propane) to $C_{30}$ paraffins. Therefore, when olefins are produced from paraffins, the heat of reactin must be supplied from an external source. The reverse is also true in that mono-olefin hydrogenation to paraffin is an exothermic reaction with the same heat of reaction. The present invention can utilize this exothermic nature of olefin hydrogenation in an alternative process scheme whereby a stream of $H_2$ deficient hydrogenatable hydrocarbons is admixed with a portion of the $H_2$ rich stream and subjected to a hydrogenation process in either a separate hydrogenation zone, containing a hydrogenation catalyst, or in the dehydrogenation zone. The product of the hydrogenation process, herein referred to as a heat providing stream is admixed with the balance of the $H_2$ rich stream and the dehydrogenatable hydrocarbon stream. If a separate hydrogenation zone is employed, it must be in the proximity of the dehydrogenation reaction zone inlet. Prior to hydrogenation, the hydrogenatable hydrocarbons may be recovered from the dehydrogenation reaction zone effluent by any suitable means, for example, as the overhead of a fractionating column. Alternatively, the hydrogenatable hydrocarbons may be introduced from an external source, for example, from the reaction products of a thermal pyrolysis process. In order to utilize the heat providing stream in such a fashion, it must be at a higher temperature than the required dehydrogenation reaction temperature. Although maintaining the heat providing stream at such a high temperature increases the tendency for the stream to thermally crack, any thermal cracking which takes place will, of course, not result in a decrease in yield of the desired product olefin. If the catalytic reaction zone comprises a series of catalyst beds, the heat providing stream may be introduced into each bed separately.

Regardless of the manner in which the reactants are introduced into the catalytic reaction zone, they are therein contacted with dehydrogenation catalysts. As indicated previously, the catalysts may be emplaced in a fixed bed, a fluidized bed, or a moving bed. Moreover, the catalytic reaction zone may consist of multiple catalyst beds. In one such system, the catalyst is emplaced within an annular bed through which it is movable via gravity flow. In such a system, it is common practice to remove catalyst from the bottom of the reaction zone, regenerate it and then return it to the top of the reaction zone.

Any suitable dehydrogenation catalyst may be used in the process of the present invention. Generally, the preferred catalyst comprises a platinum group component, an alkali metal component and a porous inorganic carrier material. The catalyst may also contain promoter metals which advantageously improve the performance of the catalyst. It is preferably that the porous carrier material of the dehydrogenation catalyst be an absorptive high surface area support having a surface are of about 25 to about 500 m$^2$/g. The porous carrier material should be relatively refractory to the conditions utilized in the reaction zone and may be chosen from those carrier materials which have traditionally been utilized in dual function hydrocarbon conversion catalysts. A porous carrier material may therefore be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxides such as alumina, titanium dioxide, zirconium dioxides, magnesia, silica alumina, alumina boria, etc,; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/16 inch.

The preferred dehydrogenation catalyst also contains a platinum group component. Of the platinum group metals, which include palladium, rhodium, ruthenium, osmium or iridium, the use of platinum is preferred. The platinum group component may exist within the final catalyst composite as a compound such as an oxide, sulfide, halide, oxysulfide, etc., or an an elemental metal or in combination with one or more other ingredients of the catalyst. It is believed that the best results are obtained when substantially all the platinum group components exists in the elemental state. The platinum group component generally comprises from about 0.01 to about 2 wt. % of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali metal may range from about 0.1 to 3.5 wt. %, but is preferably between 0.2 and about 2.5 wt. % calculated on an elemental basis. This component may be added to the catalyst by the methods described above as a separate step or simultaneously with the solution of another component. With some alkali metals, it is normally necessary to limit the halogen content to less than 0.5 wt. % and preferably less than 0.1 wt. %.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The dehydrogenation conditions which will be employed in the process of the present invention will of course vary depending on such factors as catalyst activity, feedstock, and desired conversion. A general range of conditions which may be employed for dehydrogenation of a light hydrocarbon include a temperature of from about 550° to about 800° C., a pressure of from about 0.01 to about 10 atmospheres absolute, a liquid hourly space velocity between about 0.1 and 100 hr$^{-1}$ and a hydrogen to paraffin mole ratio from about 0.01:1 to about 40:1.

The presence of the heat providing stream in the reaction zone increases the thermal inertia of the material within the reaction zone by providing heat which is liberated during hydrogenation of the hydrogenatable components of the heat providing stream and providing more mass within the reaction zone. Hence, the reactants undergo less of temperature drop as they pass through the reaction zone and under conversion to their corresponding olefins. Therefore, increased conversion of the dehydrogenatable hydrocarbons is achieved. Moreover, since the reactants undergo a reduced temperature drop through the reaction zone, it is unnecessary to heat the reactants to as high of a temperature prior to the introduction thereof to the reaction zone. Thus, thermally induced deleterious side reactions such as thermal cracking are reduced.

BRIEF DESCRIPTION OF THE DRAWINGS

In further describing the present inventive concept, reference will be made to the accompanying drawings which serve to illustrate one or more embodiments thereof. Although the drawings depict specific configurations for the catalytic dehydrogenation process, as previously set forth above, such a process may have varying configurations suited to the specific circumstances prevailing in a particular application and there is no intent to limit the broad application of the present invention to the embodiments discussed hereinafter. The figures in the drawings depict simplified schematic flow diagrams of three catalytic dehydrogenation processes based on engineering estimates and in accordance with the present invention in which only principal items and pieces of equipment are shown. Details, such as miscellaneous pumps, heaters, and coolers, condensers, startup lines, valving, and similar hardware have been omitted as being nonessential to a clear understanding of the techniques involved. The utilization of such appurtenances, to modify the illustrated process, is well within the purview of one having ordinary skills in the art, and will not remove the resulting process beyond the scope and spirit of the appended claims.

DETAILED DESCRIPTION OF THE DRAWINGS

Figure 1:
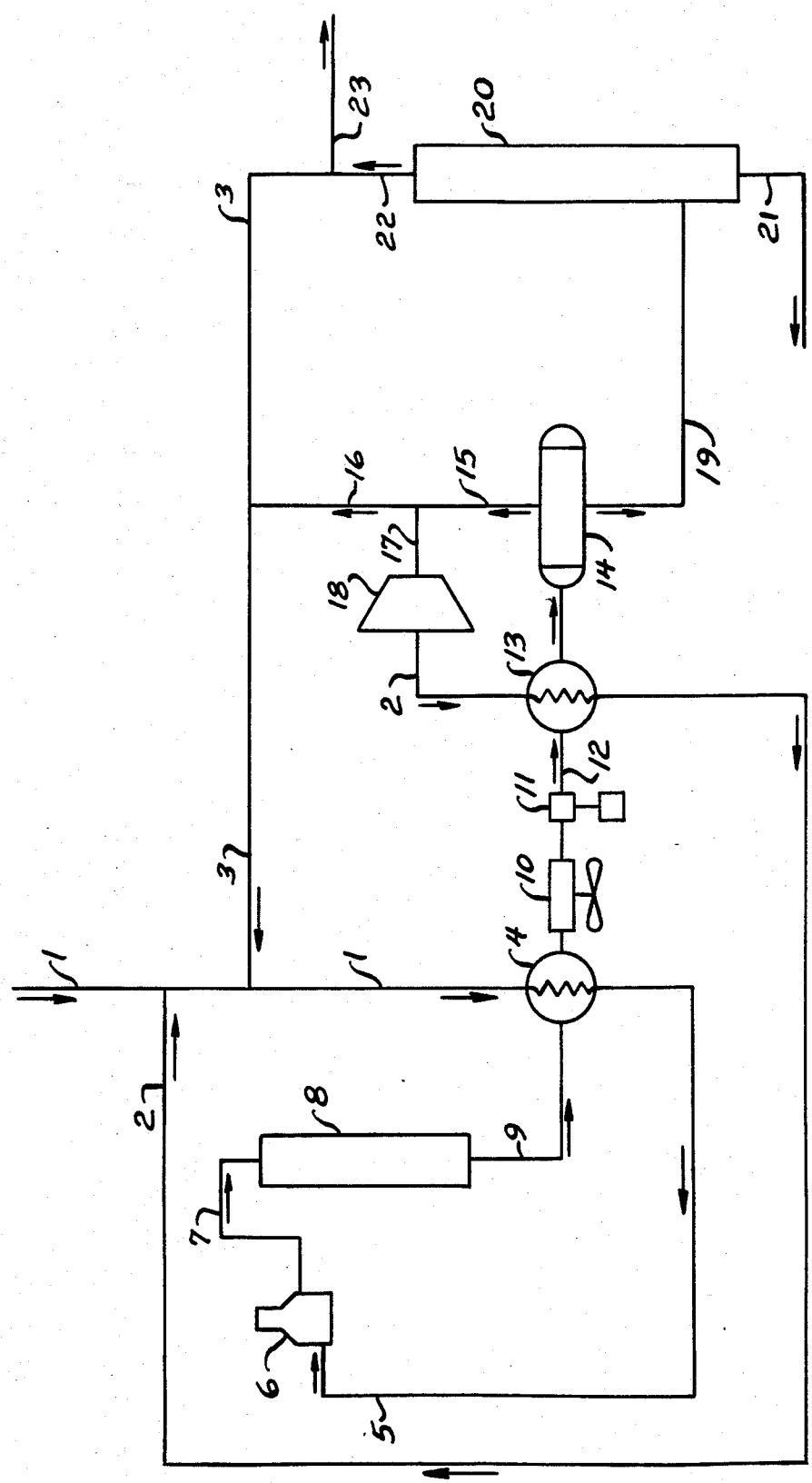

Referring specifically then to the drawing in FIG. 1, a dehydrogenatable hydrocarbon feed stream comprising propane is introduced via line 1 and admixed with a H$_2$ rich stream recycled from product separation facilities via line 2. The resulting admixture is then further admixed with a heat providing stream recycled from the overhead fractionation column 20 via line 3. The resulting admixture is then subjected to indirect heat exchange with the reaction zone effluent in heat exchange means 4. After this initial preheating, the admixture is passed to fired heater 6 via line 5 wherein it is heated to a temperature of about 650° C.

The heated admixture leaves fired heater 6 via line 7 through which it is passed to dehydrogenation reaction zone 8. The admixture heated to reaction temperature is contacted with the dehydrogenation catalyst emplaced within reaction zone 8. Reaction zone 8 has been shown as a single vessel in FIG. 1. However, as noted previously, the dehydrogenation reaction zone may have many configurations. The most advantageous configuration will of course be dictated by the specific circumstances.

The reaction zone effluent resulting from the dehydrogenation of propane is withdrawn from the reaction zone via line 9. Although the temperature of the effluent is reduced from 650° C. as a result of the endothermic dehydrogenation reaction, there is still substantial heat available which may be advantageously utilized to preheat the reaction zone feed admixture. Accordingly, the reaction zone effluent is subject to indirect heat exchange in heat exchange means 4.

After leaving heat exchange means 4, the reaction zone effluent is further cooled by indirect heat exchange with the ambient air in air cooler 10. After indirect heat exchange with air, the reaction zone effluent is compressed in reciprocating compressor 11. The increasing pressure is utilized to facilitate the separation of the reaction zone effluent into a H$_2$ rich vapor phase and a liquid phase. This separation is effected by an autorefrigeration cycle as will be explained hereinafter. After compression, the reaction zone effluent in vapor phase is passed via line 12 to heat exchange means 13. In heat exchange means 13, the reaction zone effluent is partially condensed by subjecting it to indirect heat exchange with a cold H$_2$ rich vapor phase in line 2. The reaction zone effluent, partially condensed, is withdrawn from heat exchange means 13 and passed to vapor-liquid equilibrium separation zone 14. Although separation zone 14 is depicted as a single vessel, the vapor-liquid equilibrium separation zone is of course dependent on the particular circumstances of the given application.

A H$_2$ rich vapor phase is withdrawn via line 15 from separation zone 14. A portion of the H$_2$ rich vapor phase is passed via line 17 through expander 18. As a result of the expansion undergone by he H$_2$ rich vapor phase, the temperature thereof is decreased. The now-cold H$_2$ rich vapor phase is then passed to heat exchange means 13 wherein it is subject to indirect heat exchange with the reaction zone effluent thereby chilling and condensing the effluent as previously indicated above.

After undergoing indirect heat exchange with the reaction zone effluent, the H$_2$ rich vapor phase continues on via line 2 and is admixed with the dehydrogenatable hydrocarbon feed in line 1. The balance of the H$_2$ rich vapor phase withdrawn from the vapor-liquid equilibrium separation zone is removed from the process via line 16 for advantageous use elsewhere.

A liquid phase comprising propylene, propane, ethylene, ethane, methane, and trace amounts of hydrogen is withdrawn from the vapor-liquid equilibrium separation zone via line 19. It is then passed to fractionation column 20. Since the desired product olefin is propylene, fractionation colum 20 is a deethanizing fractionation column. A first product stream comprising propylene and propane is removed from the fractionation zone via line 21 as a bottoms fraction. The bottoms stream may be further processed to separate the product propylene from unreacted propane. The propane may then be recycled and admixed with the fresh feed which enters the process via line 1.

A second product stream comprising ethane, ethylene, methane, and trace amounts of hydrogen is removed from the fractionation zone as an overhead fraction via line 22. A first portion of the second product stream amounting to about 40% by weight of the entire overhead stream is removed from the process via line 23. The balance of the overhead stream is passed via line 3 as the heat providing stream for admixture with the dehydrogenatable hydrocarbon feed, propane, and $H_2$ rich stream in line 1.

As a result of recycling the fractionation zone overhead material as the heat providing stream, the thermal inertia of the total reaction zone feed in line 7 is increased. As a result, the temperature drop experienced through the reaction zone is decreased. Concomitantly, the conversion of propane to propylene is increased. Additionally, by assuring a lower temperature drop through the reaction zone, it is less necessary to provide for intra-reaction zone addition of heat. Thus, the need for additional fired heaters for inter-catalyst bed heating of the reactants is obviated and an advantage in fuel savings is necessarily achieved thereby.

Figure 2:
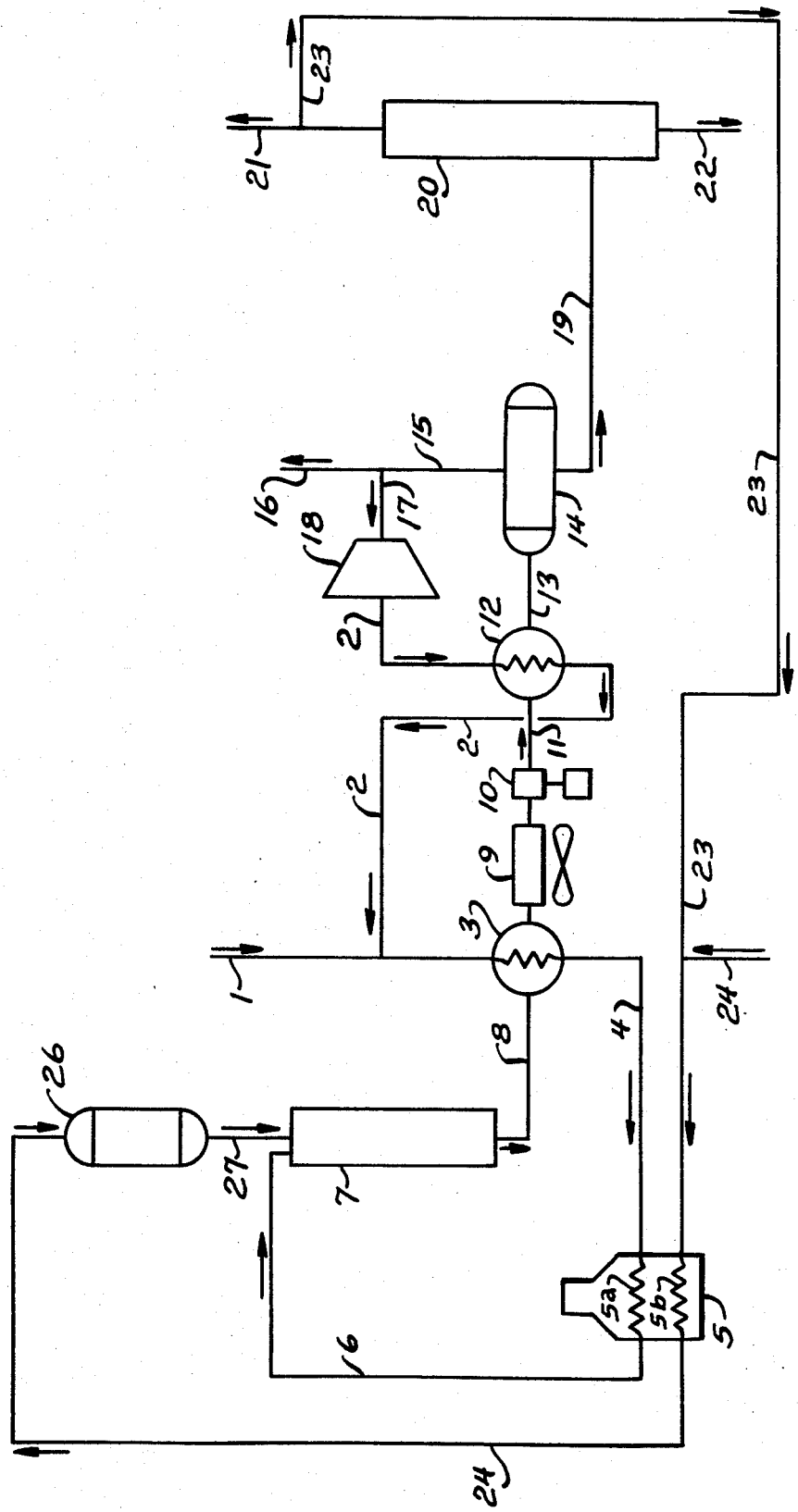

Another catalytic dehydrogenation process envisioned is depicted in FIG. 2 where a dehydrogenatable hydrocarbon stream comprising propane is introduced via line 1 and admixed with a $H_2$ rich stream recycled from product separation facilities via line 2. The resulting admixture is then subjected to indirect heat exchange with the reaction zone effluent in heat exchange means 3. After this initial preheating, the admixture is passed via line 4 to heater coil 5a within fired heater 5.

In heater coil 5a, the admixture is raised to a temperature of about 540° C., this temperature being selected to minimize thermal cracking of the light hydrocarbon. The heated admixture is removed from fired heater 5 via line 6 and is passed into dehydrogenation reaction zone 7. Although not depicted, the dehydrogenatable hydrocarbon, prior to the introduction thereof into the dehydrogenation catalyst bed, is admixed with a hydrogenated stream which is at a temperature of about 900° C. and originates from line 27. As a result, the combined $H_2$ rich dehydrogenatable hydrocarbon, and hydrogenated stream entering the dehydrogenation catalyst bed is at a temperature of about 630° C. It is, of course, to be remembered that dehydrogenation reaction zone 7 is depicted here as a single vessel. However, as noted above, the actual dehydrogenation reaction zone may have various configuration of the dehydrogenation zone.

A dehydrogenation reaction zone effluent is withdrawn from the dehydrogenation reaction zone via line 8 and thereafter is subjected to indirect heat exchange with the dehydrogenatable hydrocarbon and $H_2$ rich from line 1 in heat exchange means 3. Following the indirect heat exchange, the dehydrogenation reaction zone effluent is passed to air cooler 9 wherein the temperature of the reaction zone effluent is decreased to about 50° C. After leaving cooler 9, the dehydrogenation reaction zone effluent is compressed in reciprocating compressor 10. The increase in pressure is utilized to facilitate the separation of the reaction zone effluent into a $H_2$ rich vapor phase and a liquid phase. This separation is effected by an autorefrigeration cycle as will be explained hereinafter. After compression, the dehydrogenation reaction zone effluent in vapor phase is passed via line 11 to heat exchange means 12. In heat exchange means 12, the dehydrogenation reaction zone effluent is partially condensed by subjecting it to indirect heat exchange with a cold $H_2$ rich vapor phase in line 2. The dehydrogenation reaction zone effluent, partially condensed, is withdrawn from heat exchange means 12 and passed to vapor-liquid equilibrium separation zone 14 via line 13. Although separation zone 14 is depicted as a single vessel as noted previously, the vapor-liquid equilibrium separation zone may have various configurations consisting of one or more vessels. The exact configuration of the vapor-liquid equilibrium separation zone is, of course, dependent upon the particular circumstances of the given application.

A $H_2$ rich vapor phase is withdrawn via line 15 from separation zone 14. A portion of the $H_2$ rich vapor phase is passed via line 17 through expander 18. As a result of the expansion undergone by the $H_2$ rich vapor phase, the temperature thereof is decreased. The now cold $H_2$ rich vapor phase is then passed to heat exchange means 12 wherein it is subject to indirect heat exchange with the reaction zone effluent thereby chilling and condensing the effluent as previously indicated above. After undergoing indirect heat exchange with the reaction zone effluent, the $H_2$ rich hydrocarbon vapor phase continues on via line 2 and is admixed with the dehydrogenatable hydrocarbon feed in line 1. The balance of the $H_2$ rich vapor phase withdrawn from the vapor-liquid equilibrium separation zone 14 is removed from the process via line 16 for advantageous use elsewhere.

A liquid phase comprising propylene, propane, ethylene, ethane, methane, and trace amounts of hydrogen is withdrawn from the vapor-liquid equilibrium separation zone 14 via line 19. The liquid phase is thereafter passed to fractionation column 20. Since the desired product olefin is propylene, fractionation column 20 is a deethanizing fractionation column. A first product stream comprising propylene and propane is removed from the fractionation zone via line 22 as a bottoms fraction. The bottoms stream may be further processed to separate the product propylene from unreacted propane. The propane may then be recycled and admixed with the fresh feed which enters the process via line 1.

A second product stream comprising ethane, ethylene, methane, and trace amounts of hydrogen is removed from fractionation column 20 as an overhead fraction. A first portion of the second product stream, amounting to about 40% by weight of the entire overhead stream, is removed from the process via line 21. The balance of the overhead stream is passed for heating via line 23. Prior to heating, the second product stream is admixed with a $H_2$ rich stream which is introduced via line 24. It should be noted that the $H_2$ in line 24 may comprise net separator off-gas $H_2$ from line 16 or it may comprise $H_2$ from a totally different source. Regardless of the source of the $H_2$, the admixture is continued through line 23 to heater 5 wherein it is brought to a temperature of 600° C. in heater coil 5b. The admixture is then withdrawn from the fired heater and passed via line 24 to hydrogenation reaction zone 26. In hydrogenation reaction zone 26, the olefinic material, in this case ethylene with perhaps trace amounts of propylene, is subjected to hydrogenation in the presence of a hydrogenation catalyst. Because of the highly exothermic nature of the hydrogenation reaction, the material in hydrogenation reaction zone 26 undergoes a temperature increase. In this case, the effluent from hydrogenation reaction zone 26 is at a temperature of 800° to 900° C. depending on the olefinicity of the feed. Thus, the hydrogenation reaction zone material undergoes a temperature increase of about 200° to 300° C. The effluent from the hydrogenation reaction, herein referred to as a heat providing stream, is then withdrawn from the hydrogenation reaction zone via line 27 wherein it is passed for admixture with the hydrogenatable hydrocarbons and the $H_2$ rich recycle stream.

As a result of utilizing the heat providing stream to raise the light hydrocarbon to the dehydrogenation reaction zone inlet temperature just prior to the introduction thereof into the dehydrogenation reaction zone, there is an overall decrease in the amount of thermal crracking experienced by the dehydrogenatable hydrocarbon. Moremover, the increase of mass within the dehydrogenation reaction zone results in a decrease in the temperature drop experienced by the dehydrogenation reaction zone material. Concomitantly, the conversion of propane to propylene is increased. Additionally, by assuring a lower temperature drop through the dehydrogenation reaction zone, is a reduction in the need for intra-reaction zone addition of heat.

Figure 3:
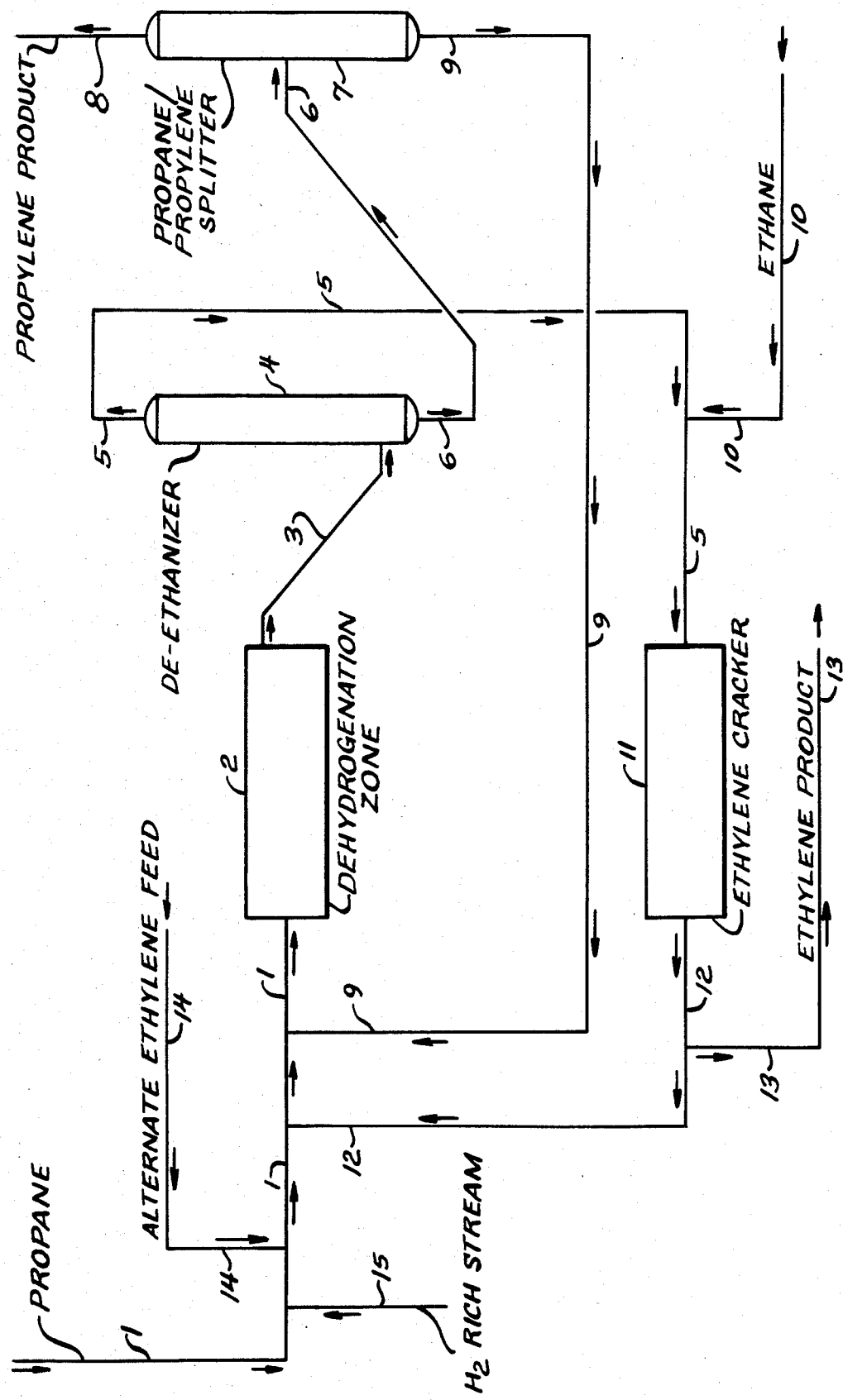

A third possible catalytic dehydrogenation process, which is depicted in FIG. 3, uses the olefinic reaction products from a thermal pyrolysis process, shown herein as an ethylene cracker. The dehydrogenatable hydrocarbon stream comprising propane is introduced via line 1 and admixed with a $H_2$ rich stream via line 15. Although not depicted, the $H_2$ rich stream of line 15 may originate from the dehydrogenation reaction effluent product separation facilities, not shown, or it may originate from an entirely different source. The dehydrogenatable hydrocarbon and $H_2$ rich admixture is then admixed with the olefinic stream, comprising ethylene obtained from either thermal pyrolysis product stream 12 or an alternate source 14. The resulting admixture is then introduced into the dehydrogenation reaction zone 2. The effluent from dehydrogenation zone 2 comprising propane, propylene, ethane and ethylene is passed via line 3 into deethanizer 4. A hydrocarbon stream rich in ethane and ethylene is removed from the overhead of deethanizer 4 via line 5 and introduced together with an ethane stream provided by line 10 into ethylene cracker 11. An effluent stream comprising ethylene is removed from ethylene cracker 11 via line 12 and introduced into dehydrogenation zone 2 via lines 12 and 1 as hereinabove described. The net ethylene product from ethylene cracking 11 is recovered via lines 12 and 13. A hydrocarbon stream comprising propane and propylene is removed from the bottom of deethanizer 4 via line 6 and introduced into propane/propylene splitter 7. A propylene product stream is removed from the top of propane/propylene splitter 7 via line 8. A propane stream is removed from the bottom of propane/propylene splitter 7 via line 9 and introduced into dehydrogenation 2 via lines 9 and 1.

In the dehydrogenation reaction zone 2 the olefinic stream reacts with the hydrogen in the $H_2$ rich stream thereby forming the corresponding paraffin, herein referred to as a heat providing stream. This paraffin formation and corresponding heat liberation increases the mass within the dehydrogenation reaction zone and minimizes the drop in temperature of reactants as they undergo the dehydrogenation reaction. Concomitantly, the conversion of propane to propylene is increased. Additionally, by assuring a lower temperature drop through the dehydrogenation reaction zone is a reduction in the need for intra-reaction addition of heat.

The following example is given to illustrate further the process of the present invention and the use thereof for the dehydrogenation of hydrocarbons. The example is not to be construed as an undue limitation on the generally broad scope of the invention as set out in the appended claims and is therefore intended to be illustrative rather than restrictive.

EXAMPLE

A small scale hydrocarbon dehydrogenation plant was selected and loaded with a hydrogenation catalyst which contained platinum, tin and potassium on a carrier of gammaalumina. A hydrocarbon feed stream containing essentially pure isobutane was combined with a hydrogen gas stream and the resulting mixture was heated to the desired conversion temperature which is measured at the inlet to the dehydrogenation reactor. The heated mixture was then contacted with the fixed bed of catalyst contained in the plant. An effluent stream was withdrawn from the reactor and cooled. A portion of the effluent stream was collected and analyzed to measure the amount of conversion of isobutane, or activity, and the relative amount of desired isobutylene or selectivity. Conversion numbers reported herein are calculated on the basis of disappearance of isobutane, expressed in weight percent of the feed stream. Similarly, selectivity numbers reported are calculated on the basis of desired isobutylene produced, expressed in mole percent, of the isobutane converted. During the first test run with a charge stock or feed stream of isobutane, the conversion was found to be 22.7 weight percent of the isobutane while attaining an isobutylene selectivity of 90.8 mole percent. These results are presented in Table 1.

A second test run was performed utilizing the same dehydrogenation plant and catalyst as described herein above. The second test was conducted with a feed stream containing isobutane and an amount of ethylene sufficient to provide an isobutane/ethylene molar ratio of 3.6:1. The reaction conditions were the same for both tests and which conditions included a reactor inlet temperature of 1120° F., equal isobutane flow rates, a pressure of about two atmospheres, a hydrogen to isobutane mole ratio of about 2:1 and a liquid hourly space velocity (LHSV) of about 10 $hr^{-1}$. The second test which is a preferred embodiment of the present invention demonstrated a conversion of 30.1 weight percent of the isobutane while attaining an isobutylene selectivity of 94.8 mole percent. These results are also presented in Table 1.

TABLE I

ISOBUTANE DEHYDROGENATION

| Reactor Feed | Isobutane Conversion Weight Percent | Isobutylene Selectivity Mol Percent |
|---|---|---|
| Isobutane | 22.7 | 90.8 |
| Isobutane/Ethylene (3.6:1 molar ratio) | 30.1 | 94.8 |

A comparison of the results of the first test run or control with the results of the second test run clearly shows the superiority of the process conducted in the second test run whereby the isobutane conversion was 32% greater and the isobutylene selectivity was 4.4% greater than the control case.

The foregoing description and example clearly illustrate the improvements encompassed by the present invention and the benefits to be afforded with the use of the process of the present invention.

What is claimed is:

1. A process for dehydrogenating $C_3$-$C_4$ paraffins in a dehydrogenation reaction zone containing dehydrogenation catalyst comprising the steps of:
   (a) heating the $C_3$-$C_4$ paraffins and a $H_2$-rich stream comprising at least 75 mole % $H_2$ to a temperature less than the dehydrogenation reaction zone inlet temperature;
   (b) hydrogenating a stream of $H_2$ deficient hydrogenatable hydrocarbons comprising $C_2$-$C_3$ hydrocarbons and less than 5 mole % $H_2$ in the presence of a hydrogenation catalyst at a temperature of at least 600° C.;
   (c) utilizing the exothermic heat of reaction obtained from the hydrogenated $H_2$ deficient stream hereinafter referred to as a heat providing stream by admixing the heat providing stream with the $C_3$-$C_4$ paraffins and $H_2$-rich stream in the proximity of the dehydrogenation zone inlet to raise the temperature of the $C_3$-$C_4$ paraffins and $H_2$-rich stream to the dehydrogenation reaction zone inlet temperature;
   (d) contacting the thusly heated $C_3$-$C_4$ paraffins, $H_2$-rich stream and heat providing stream with dehydrogenation catalyst in the reaction zone to produce a dehydrogenation reaction zone effluent;
   (e) separating the effluent into a $H_2$-rich vapor phase and a liquid phase;
   (f) recycling at least a portion of the $H_2$-rich vapor phase for use as the $H_2$-rich stream;
   (g) separating the liquid phase in a fractionation column to produce a first product stream comprising the dehydrogenated hydrocarbons and a second stream comprising hydrocarbons having less carbon atoms per molecule than the $C_3$-$C_4$ paraffins;
   (h) recycling at least a portion of the second stream for use as the $H_2$ deficient hydrogenatable hydrocarbons of step (b).

2. The process of claim 1 further characterized in that at least a portion of the $H_2$-rich vapor phase of step (d) is contacted with the $H_2$ deficient hydrogenatable hydrocarbons in the presence of the hydrogenation catalyst.

* * * * *